United States Patent
Kamikawa et al.

(10) Patent No.: US 10,272,565 B2
(45) Date of Patent: Apr. 30, 2019

(54) MOTOR, ACTUATOR, AND MEDICAL SUPPORT ARM APPARATUS

(71) Applicant: SONY CORPORATION, Tokyo (JP)

(72) Inventors: Yasuhisa Kamikawa, Tokyo (JP); Tetsuharu Fukushima, Tokyo (JP); Wataru Kokubo, Tokyo (JP); Toshimitsu Tsuboi, Tokyo (JP); Yohei Kuroda, Tokyo (JP); Jun Arai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 62 days.

(21) Appl. No.: 15/549,264

(22) PCT Filed: Jan. 8, 2016

(86) PCT No.: PCT/JP2016/050516
§ 371 (c)(1),
(2) Date: Aug. 7, 2017

(87) PCT Pub. No.: WO2016/136298
PCT Pub. Date: Sep. 1, 2016

(65) Prior Publication Data
US 2018/0036877 A1  Feb. 8, 2018

(30) Foreign Application Priority Data

Feb. 27, 2015  (JP) ................ 2015-038495

(51) Int. Cl.
*H02P 6/12* (2006.01)
*B25J 9/10* (2006.01)
(Continued)

(52) U.S. Cl.
CPC ............... *B25J 9/102* (2013.01); *A61B 34/00* (2016.02); *A61B 90/00* (2016.02); *A61B 90/50* (2016.02);
(Continued)

(58) Field of Classification Search
CPC ................... H02P 5/00; H02P 29/40; G05B 2219/403991; B25J 9/102
See application file for complete search history.

(56) References Cited

U.S. PATENT DOCUMENTS 4,175,727 A * 11/1979 Clarke ............... B66D 5/26
  192/12 R
2003/0218720 A1 * 11/2003 Morita ............... A61B 1/00048
  351/222

(Continued)

FOREIGN PATENT DOCUMENTS

| JP | 2002-095293 A | 3/2002 |
| JP | 2002-95293 A | 3/2002 |

(Continued)

OTHER PUBLICATIONS

International Search Report and Written Opinion of PCT Application No. PCT/JP2016/050516, dated Mar. 8, 2016, 02 pages of English Translation and 07 pages of ISRWO.

*Primary Examiner* — Karen Masih
(74) *Attorney, Agent, or Firm* — Chip Law Group (57) ABSTRACT

Provided is an actuator, including: a motor; and a reduction gear having a breakdown torque that is less than a starting torque of the motor. A limit value in accordance with the breakdown torque of the reduction gear is set with respect to a control value for driving the motor.

16 Claims, 6 Drawing Sheets

(51) Int. Cl.
    *B25J 19/06*     (2006.01)
    *H02P 29/00*     (2016.01)
    *A61B 90/00*     (2016.01)
    *A61B 34/00*     (2016.01)
    *H02P 29/40*     (2016.01)
    *B25J 19/02*     (2006.01)
    *A61B 90/50*     (2016.01)
    *A61B 90/35*     (2016.01)
    *A61B 90/25*     (2016.01)

(52) U.S. Cl.
    CPC ............. *B25J 19/023* (2013.01); *B25J 19/06* (2013.01); *H02P 29/00* (2013.01); *H02P 29/40* (2016.02); *A61B 34/70* (2016.02); *A61B 90/25* (2016.02); *A61B 90/35* (2016.02)

(56) References Cited

U.S. PATENT DOCUMENTS

| | | | | |
|---|---|---|---|---|
| 2013/0143676 | A1* | 6/2013 | Numata | F16D 3/64 464/77 |
| 2017/0258549 | A1* | 9/2017 | Tamura | A61B 90/37 |
| 2017/0351243 | A1* | 12/2017 | Sawada | G05B 19/4065 |

FOREIGN PATENT DOCUMENTS

| | | |
|---|---|---|
| JP | 2003-135883 A | 5/2003 |
| JP | 2008-072787 A | 3/2008 |
| JP | 2012-090494 A | 5/2012 |
| JP | 2012-90494 A | 5/2012 |
| JP | 2012-218553 A | 11/2012 |
| JP | 2015-033220 A | 2/2015 |
| JP | 2015-33220 A | 2/2015 |

\* cited by examiner

MOTOR, ACTUATOR, AND MEDICAL SUPPORT ARM APPARATUS

CROSS REFERENCE TO RELATED APPLICATIONS

This application is a U.S. National Phase of International Patent Application No. PCT/JP2016/050516 filed on Jan. 8, 2016, which claims priority benefit of Japanese Patent Application No. JP 2015-038495 filed in the Japan Patent Office on Feb. 27, 2015. Each of the above-referenced applications is hereby incorporated herein by reference in its entirety.

TECHNICAL FIELD

The present disclosure relates to a motor, an actuator, and a medical support arm apparatus.

BACKGROUND ART

An actuator for driving a rotating mechanism, such as a joint unit of a robot apparatus or an electric power steering apparatus for an automobile, is made up of parts such as a motor, a reduction gear, a shaft, and a torque sensor. With regard to actuators, technology that controls the driving of the motor so as not to break these component parts is being developed.

For example, Patent Literature 1 discloses a technology for an electric power steering apparatus of an automobile that measures a count of the number of times a steering wheel reaches a maximum steering angle and a rack hits a stopper (end-hit count), and in a case in which the end-hit count reaches a certain count, a limit is set on a current command value for driving the motor.

As another example, Patent Literature 2 discloses a technology for a servo motor used in an actuator that limits the current flowing to the servo motor in accordance with the temperature of a coil in the servo motor.

CITATION LIST

Patent Literature

Patent Literature 1: JP 2012-218553A
Patent Literature 2: JP 2008-72787A

DISCLOSURE OF INVENTION

Technical Problem

Here recently, in the medical field, support arm apparatus are being used to support surgeries and examinations. For example, a method is proposed in which an observation unit such as a camera for observing a surgical site is provided on the front edge of an arm unit of a support arm apparatus, and the surgeon performs surgery while viewing an image captured by the observation unit. In a medical support arm apparatus, an actuator is provided in a joint unit constituting the arm unit and configured to enable driving of the arm unit, and in such a medical support arm apparatus including an actuator, from a safety perspective, there is also demand for the inclusion of technology that prevents breakdown of the actuator as above.

On the other hand, if usage in the medical field is considered, there is demand for the arm unit of the support arm apparatus to be more compact. This is because if the configuration of the arm unit is large, there is a risk that the workspace of the surgeon performing surgery and the surgeon's field of view may be limited by the arm unit, thereby inhibiting smooth work.

In this way, in an actuator provided in a joint unit of a medical support arm apparatus, there is demand for technology that achieves both greater compactness and more reliable prevention of breakdown.

Herein, with the technologies described in Patent Literature 1 and 2 above, for example, it is conceivable that actuator breakdown can be prevented suitably, but the compactness of the actuator is not particularly investigated. In this case, technology that prevents breakdown for a compact actuator has not been fully investigated thus far.

Accordingly, the present disclosure proposes a new and improved actuator and medical support arm apparatus enabling greater compactness and also capable of preventing breakdown more reliably.

Solution to Problem

According to the present disclosure, there is provided an actuator, including: a motor; and a reduction gear having a breakdown torque that is less than a starting torque of the motor. A limit value in accordance with the breakdown torque of the reduction gear is set with respect to a control value for driving the motor.

Further, according to the present disclosure, there is provided a medical support arm apparatus, including: an arm unit made up of a plurality of joint units; and a medical tool provided on a front edge of the arm unit. An actuator provided in the joint unit includes a motor, and a reduction gear having a breakdown torque that is less than a starting torque of the motor, and a limit value in accordance with the breakdown torque of the reduction gear is set with respect to a control value for driving the motor.

According to the present disclosure, in an actuator, a reduction gear having a breakdown torque that is less than the starting torque of the motor is used. Consequently, a more compact reduction gear may be used, and the actuator may be made more compact. Also, in the driving control of the actuator, a limit value in accordance with the breakdown torque of the reduction gear is set with respect to the control value for driving the motor. Consequently, even if a reduction gear having a breakdown torque that is less than the starting torque of the motor is used, breakdown of the reduction gear may be prevented.

Advantageous Effects of Invention

According to the present disclosure as described above, greater compactness and also more reliable prevention of breakdown become possible. Note that the effects described above are not necessarily limited, and along with or instead of the effects, any effect that is desired to be introduced in the present specification or other effects that can be expected from the present specification may be exhibited.

MODE(S) FOR CARRYING OUT THE INVENTION

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

Hereinafter, the description will proceed in the following order.
1. Investigation of Typical Support Arm Apparatus
2. Overview of Support Arm Apparatus
3. Configuration of Support Arm Apparatus
   3-1. Overall Configuration
   3-2. Configuration of Actuator
4. Actuator Driving Control Method
5. Breakdown Torque
6. Supplement (1. Investigation of Typical Support Arm Apparatus)

Before describing one preferred embodiment of the present disclosure in detail, the results of investigation by the inventors into a typical support arm apparatus including an actuator and configured to enable driving will be described. Note that in the following description, the case of simply referring to a support arm apparatus, unless specifically noted otherwise, is taken to mean a support arm apparatus which is provided with an actuator in at least one of the joint units constituting the arm unit, and which is configured to enable driving of the arm unit by the actuator.

Recently, in the medical field, support arm apparatuses are being used to support surgeries and examinations. In such a support arm apparatus for medical use, there is demand for the arm unit to be more compact. This is because if the configuration of the arm unit is large, there is a risk that the workspace of the surgeon performing surgery and the surgeon's field of view may be limited by the arm unit, thereby inhibiting smooth work.

Accordingly, with regard to a support arm apparatus, the inventors conducted an investigation into technology for realizing a more compact arm unit.

To make an arm unit more compact, it is effective to make the actuator provided in each joint unit of the arm unit more compact. On the other hand, typically, when designing an actuator, the component parts of the actuator (such as the motor, reduction gear, shaft, and torque sensor) are chosen so that the breakdown torque of each component part is greater than the starting torque of the motor, so that the component parts do not break down during driving.

Note that herein, breakdown torque does not necessarily mean a torque at which breakdown is reached by exceeding that torque only once. The breakdown torque may also be a torque decided on the basis of the fatigue failure characteristics of each component member, for example, and may be a torque at which breakdown is reached in a case in which a component member is used for a certain amount of time under the load of that torque. The breakdown torque of each component member may be set appropriately for each component member by a person such as the designer of the actuator, with consideration for the fatigue life demanded of the actuator. The breakdown torque will be described further in (5. Breakdown torque) below with reference to FIG. 6.

In the case of attempting to increase the breakdown torque, each component part naturally becomes larger in size. Consequently, when designing the actuator, the breakdown torque and relationships demanded of the breakdown torque as above become design constraints, making it difficult to realize a compact actuator.

In particular, as a result of actually doing design work, the inventors learned that the size of the reduction gear may greatly influence the size of the actuator. In other words, the inventors learned that if the reduction gear is chosen so that the breakdown torque of the reduction gear is greater than the starting torque of the motor, a bulky reduction gear must be used, and correspondingly, the actuator likewise becomes more bulky.

Also, given the above design concepts, the torque sensor provided in the actuator likewise is chosen so that its breakdown torque is greater than the starting torque of the motor. However, having a large breakdown torque means being resistant to deformation to the same degree. Typically, since a torque sensor detects torque on the basis of the amount of deformation of a member using a strain gauge, a torque sensor having a large breakdown torque tends to have low sensitivity.

In this way, from the results of investigation, the inventors learned that if typical design techniques are followed to configure an actuator under the constraint condition of having the breakdown torque of each component part be greater than the starting torque of the motor, the reduction gear in particular becomes bulky, thereby making it difficult to make the actuator more compact. Also, the inventors learned that if the torque sensor is chosen in accordance with the above constraint condition, there is a possibility that a torque sensor with comparatively low sensitivity must be used.

In light of the above circumstances, in an actuator provided in each joint unit of a support arm apparatus for medical use, a technology that makes the configuration more compact while also preventing breakdown of each component member has not been established. Accordingly, as a result of thorough investigation into technology that achieves both prevention of breakdown of each component member of an actuator as well as greater compactness of the configuration of the actuator, the inventors conceived the preferred embodiment of the present disclosure indicated below. The following describes in detail a preferred embodiment of the present disclosure conceived by the inventors.

(2. Overview of Support Arm Apparatus)

Before describing in detail a configuration of a support arm apparatus according to the present embodiment, an overview of a support arm apparatus according to the present embodiment will be described with reference to FIG. 1. A support arm apparatus according to the present embodiment is a medical support arm apparatus, and may be applied favorably to medical procedures such as surgeries and examinations. Herein, an example of the support arm apparatus according to the present embodiment being applied to surgery will be described, while in addition, the properties demanded of a medical support arm apparatus will be reviewed.

A state of surgery using a support arm apparatus according to the present embodiment will be described with reference to FIG. 1. FIG. 1 is a schematic diagram illustrating a state of surgery using a support arm apparatus according to the present embodiment.

Figure 1:
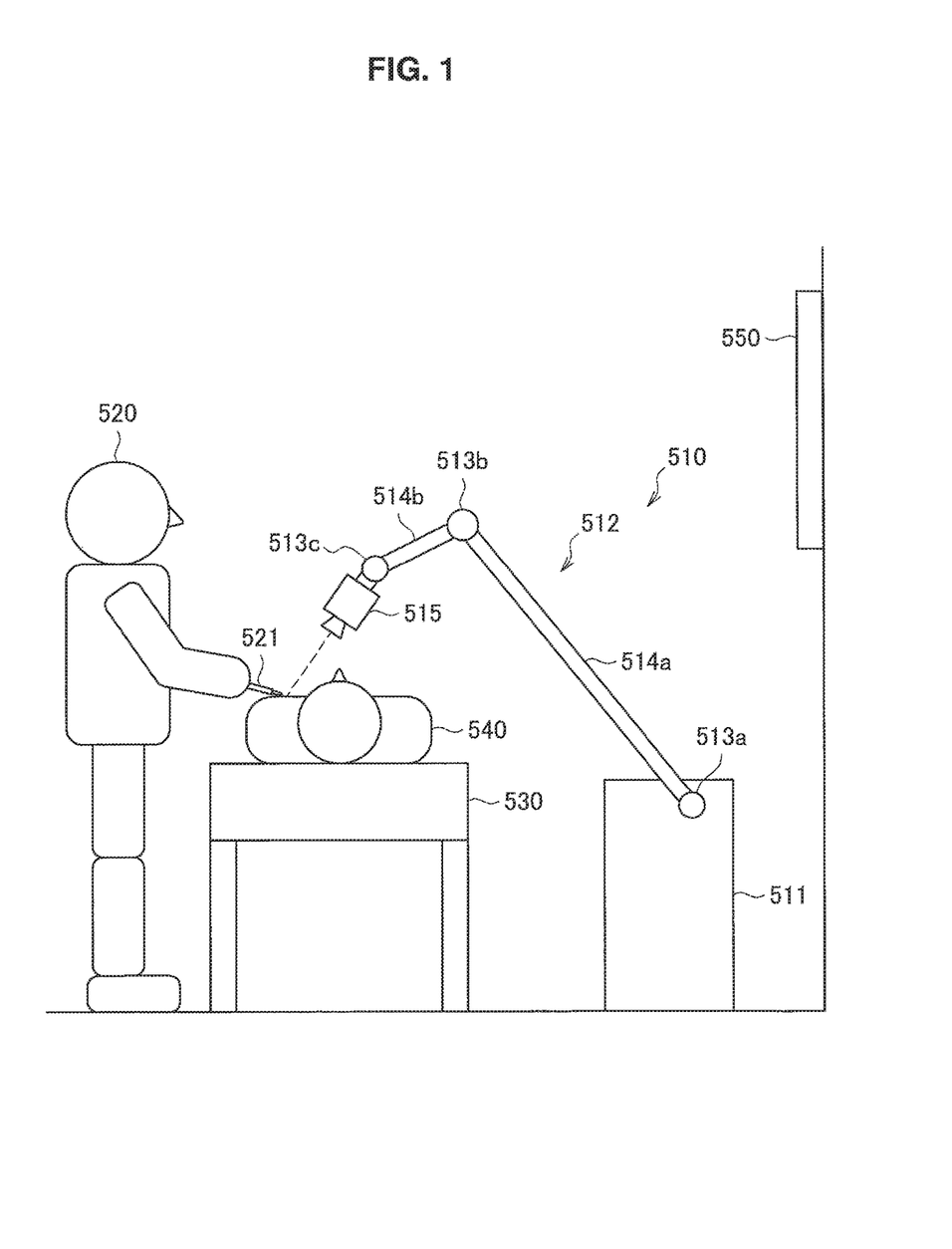
FIG. 1 is a schematic diagram illustrating a state of surgery using a support arm apparatus according to an embodiment.

FIG. 1 illustrates a state in which a surgeon 520 is using a surgical treatment tool 521, such as a scalpel, tweezers, or forceps, for example, to perform surgery on a patient 540 lying on an operating table 530. Beside the operating table 530, a support arm apparatus 510 according to the present embodiment is provided. The support arm apparatus 510 is equipped with a base unit 511 which acts as a base, and an arm unit 512 which extends from the base unit 511. Also, although omitted from illustration, the support arm apparatus 510 is equipped with a control device that controls the operation of the support arm apparatus 510 (corresponding to the control device 440 illustrated in FIG. 2 to be described later).

The arm unit 512 includes multiple joint units 513a, 513b, and 513c, multiple links 514a and 514b joined by the joint units 513a and 513b, and an imaging unit 515 joined to the front edge of the arm unit 512. The joint units 513a to 513c are provided with an actuator 430 illustrated in FIG. 3 to be described later, and the joint units 513a to 513c are configured to be rotatable about a certain rotary shaft according to the actuator 430. By controlling the driving of the actuator 430 with the above control device, the rotational angle of each of the joint units 513a to 513c is controlled, and the driving of the arm unit 512 is controlled.

Note that FIG. 1 illustrates a simplified configuration of the arm unit 512 for the sake of simplicity, but in actuality, factors such as the numbers of the joint units 513a to 513c and the links 514a and 514b, their arrangement, and the directions of the drive shafts (rotary shafts) of the joint units 513a to 513c, may be set appropriately so that the arm unit 512 has the desired degrees of freedom. For example, the arm unit 512 preferably may be configured to have six or more degrees of freedom. As a result, it becomes possible to move the imaging unit 515 freely within the movable range of the arm unit 512.

The imaging unit 515 is an example of an observation unit for observing the surgical site of the patient 540, and is a device such as a camera capable of capturing a moving image and/or a still image of an imaging target, for example. Other examples of the observation unit include an endoscope or a microscope. In this specification, a support arm apparatus in which such an observation unit that observes the surgical site of the patient 540 is provided on the front edge of the arm unit 512 is also called an observation device.

When performing surgery, as illustrated in FIG. 1, the position and the orientation of the arm unit 512 and the imaging unit 515 are controlled by the support arm apparatus 510 so that the imaging unit 515 provided on the front edge of the arm unit 512 captures an image of the surgical site of the patient 540. In the operating room, a display device 550 is installed at a position facing the surgeon 520, and an image of the surgical site captured by the imaging unit 515 is displayed on the display device 550. The surgeon 520 performs various treatments while observing the image of the surgical site displayed on the display device 550.

Note that the front edge unit provided on the front edge of the arm unit 512 is not limited to an observation unit such as the imaging unit 515, and may also be any of various types of medical tools. Such medical tools may include various operating tools, such as forceps and retractors, for example, besides the observation unit described above. In the past, since these medical tools were manipulated manually, surgery required a large number of medical staff, but by having the support arm apparatus 510 manipulate these medical tools, it becomes possible to perform surgery with fewer people.

The above thus describes a state of surgery using the support arm apparatus 510 according to the present embodiment with reference to FIG. 1. In the example illustrated in FIG. 1, the support arm apparatus 510 is used for surgery, but in cases in which a unit used for examination, such as an endoscope, is provided as the front edge unit, for example, the support arm apparatus 510 may also be used for the purpose of examination.

Herein, in the support arm apparatus 510 for medical use as described above, the arm unit 512 is taken to be positioned near the surgical site during surgery or examination. Consequently, if the configuration of the arm unit 512 is large, there is a possibility that the workspace of the surgeon 520 may become limited, and performing treatment smoothly may become difficult. Also, as illustrated in the drawing, in the case in which the surgeon 520 performs surgery while referring to an image on the display device 550, since the arm unit 512 may be positioned in between the surgeon 520 and the display device 550, if the configuration of the arm unit 512 is large, there is a risk that the visual field of the surgeon 520 observing the display device 550 may become obstructed, and the work of the surgeon 520 may be inhibited.

In this way, in order to perform surgery or examination more smoothly, there is demand for the arm unit 512 of the support arm apparatus 510 for medical use to be more compact. As a result of thorough investigation in light of the above circumstances, the inventors conceived the support arm apparatus 510 according to a preferred embodiment of the present disclosure.

Although described in detail later in (3-2. Configuration of actuator) and (4. Actuator driving control method) below, in the support arm apparatus 510 according to the present embodiment, in the actuator 430 provided in each of the joint units 513a to 513c, a reduction gear having a breakdown torque that is less than the starting torque of the motor is used. By using a reduction gear with a small breakdown torque, the reduction gear may be made more compact, thereby making it possible to make the actuator 430 more compact. Consequently, greater compactness of each of the joint units 513a to 513c may be realized, and a support arm apparatus 510 including a more compact arm unit 512 that is particularly suited to medical use may be realized.

Also, in the present embodiment, at this point, at the same time, a limit value in accordance with the breakdown torque of the reduction gear is set with respect to the control value for driving the motor. Consequently, the driving of the actuator 430 may be controlled so that the control value becomes less than or equal to the limit value, and thus even in a case of using a reduction gear having a breakdown torque that is less than the starting torque of the motor, it is possible to keep the output torque of the motor from exceeding the breakdown torque of the reduction gear, and prevent breakdown of the reduction gear.

Note that, likewise for other component members other than the reduction gear, members having a breakdown torque that is less than the starting torque of the motor may be used similarly. With this arrangement, the actuator 430 may be made even more compact. Also, in the case of using a torque sensor with a smaller breakdown torque, the torque detection accuracy of the actuator 430 may be improved. However, in this case, the driving of the actuator 430 may be controlled after first additionally setting limit values in accordance with the breakdown torques of these component members with respect to the control value for driving the motor. With this arrangement, breakdown of the actuator may be favorably prevented.

Note that in this specification, a control value with respect to the motor may mean any of various types of physical quantities that may specify the driving amount of the motor, which is computed to control the driving of the motor. For example, in a case in which the control method illustrated in FIG. 5 described later is used, a torque command value $\tau$ and a torque target value $\tau^{ref}$, as well as a current command value and a current target value obtained by converting these to current values, may be control values for driving the motor.

Hereinafter, a configuration of a support arm apparatus 510 according to the present embodiment will be described in further detail.

(3. Configuration of Support Arm Apparatus)

(3-1. Overall Configuration)

Figure 2:
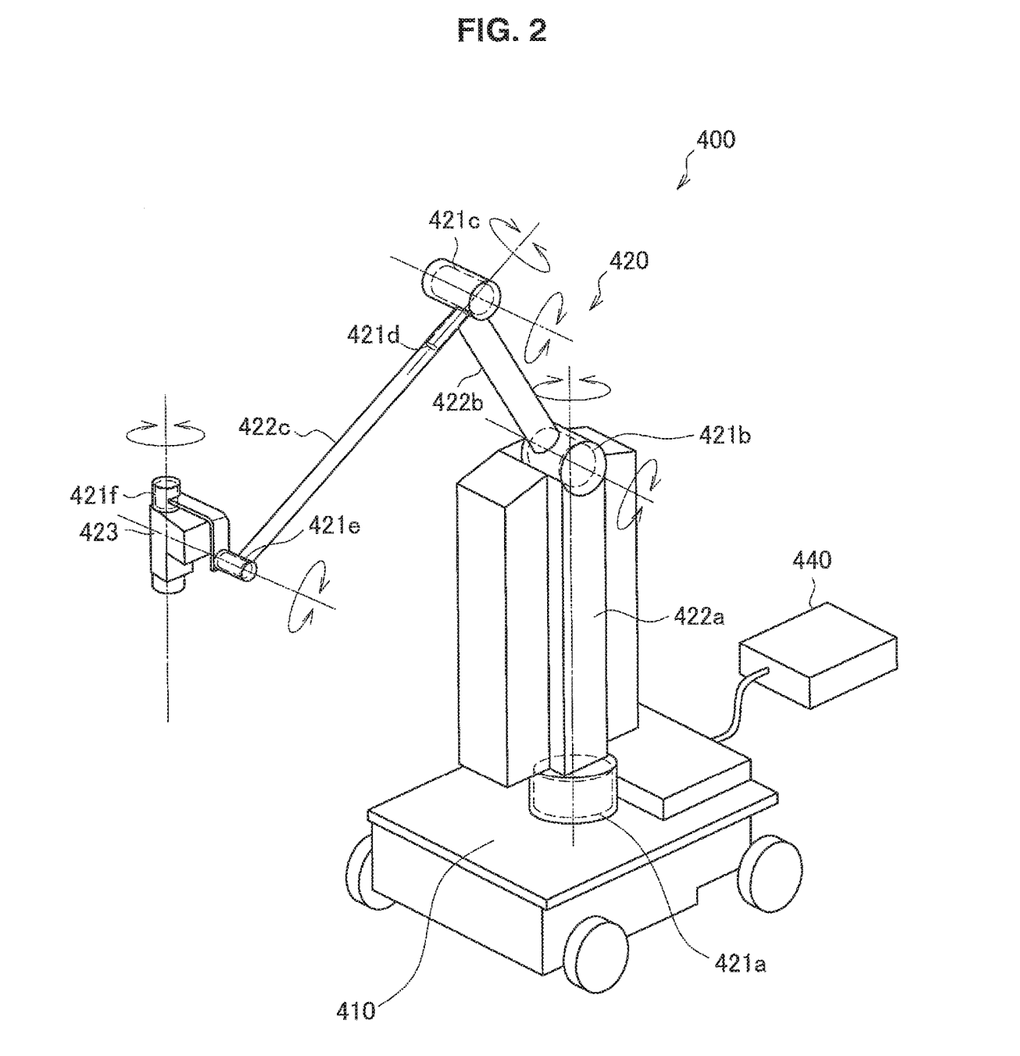
FIG. 2 is a diagram illustrating an overall configuration of a support arm apparatus according to the present embodiment.

An overall configuration of a support arm apparatus according to the present embodiment will be described with reference to FIG. 2. FIG. 2 is a diagram illustrating an overall configuration of a support arm apparatus according to the present embodiment.

Referring to FIG. 2, the support arm apparatus 400 is equipped with a base unit 410, an arm unit 420, and a control device 440. Similarly to the support arm apparatus 510 illustrated in FIG. 1 described above, the support arm apparatus 400 is a medical support arm that may be applied favorably to procedures such as surgeries and examinations.

Referring to FIG. 9, the support arm apparatus 400 is equipped with a base unit 410, an arm unit 420, and a control device 430. Similarly to the support arm apparatus 510 illustrated in FIG. 8 described above, the support arm apparatus 400 is a medical support arm apparatus that may be applied favorably to procedures such as surgeries and examinations. However, the configuration of the support arm apparatus 400 according to the present embodiment is not limited to such an example. For example, a support arm apparatus 400 may be configured in which the base unit 410 is not provided, and the arm unit 420 is attached directly to the ceiling or a wall of the operating room. For example, in the case in which the arm unit 420 is attached to the ceiling, the support arm apparatus 400 is configured so that the arm unit 420 hangs down from the ceiling.

The arm unit 420 includes a plurality of joint units 421a to 421f, a plurality of links 422a to 422c that are connected with one another by the joint units 421a to 421f, and an imaging unit 423 installed at the front edge of the arm unit 420.

The links 422a to 422c are rod-like members, one end of the link 422a is connected with the base unit 410 through the joint unit 421a, the other end of the link 422a is connected with one end of the link 422b through the joint unit 421b, and the other end of the link 422b is connected with one end of the link 422c through the joint units 421c and 421d. Further, the imaging unit 423 is connected to the front edge of the arm unit 420, that is, the other end of the link 422c through the joint units 421e and 421f. As described above, the arm shape extending from the base unit 410 is configured such that the base unit 410 serves as a support point, and the ends of the plurality of links 422a to 422c are connected with one another through the joint units 421a to 421f.

The imaging unit 423 is an example of an observation unit for observing a surgical site, and is a device such as a camera capable of capturing a moving image and/or a still image of an imaging target, for example. The imaging unit 423 corresponds to the imaging unit 515 illustrated in FIG. 1 described above. An image of the patient's surgical site captured by the imaging unit 423 is displayed on a display device (not illustrated) provided in the operating room, for example, and the surgeon performs surgery while observing the image of the patient's surgical site displayed on the display device. In this way, the support arm apparatus 400 may be an observation apparatus 400 in which an observation unit is attached to the front edge of the arm unit 420. As described earlier, devices such as an endoscope or a microscope, for example, may also be provided as the observation unit.

However, the front edge unit provided on the front edge of the arm unit 420 is not limited to an observation unit, and any of various types of medical tools may be attached to the front edge of the arm unit 420 as the front edge unit. For example, any of various types of treatment tools, such as forceps or a retractor, may be connected as the front edge unit. Alternatively, a light source for an endoscope or a microscope, or a surgical energy device used to seal blood vessels, for example, may be connected as the front edge unit.

The joint units 421a to 421f are provided with an actuator 430 illustrated in FIG. 3 to be described later, and the joint units 421a to 421f are configured to be rotatable about a certain rotary shaft according to the driving of the actuator 430. The driving of the actuator 430 is controlled by the control device 440. By respectively controlling the driving of the actuator 430 in each of the joint units 421a to 421f, driving of the arm unit 420 is controlled so as to extend or contract (fold up) the arm unit 420, for example.

Note that in the example illustrated in the drawing, the support arm apparatus 400 includes six joint units 421a to 421f, and six degrees of freedom are realized with respect to the driving of the arm unit 420. By configuring the arm unit 420 to have six degrees of freedom, the imaging unit 423 may be moved freely within the movable range of the arm unit 420. Consequently, it becomes possible to use the imaging unit 423 to image the surgical site from a variety of angles and distances. However, the configuration of the arm unit 420 is not limited to the example illustrated in the drawing, and factors such as the numbers of the joint units 421a to 421f and the links 422a to 422c, their arrangement, and the directions of the drive shafts of the joint units 421a to 421f, may be set appropriately so that the arm unit 420 has the desired degrees of freedom. However, in consideration of freedom in the position and the orientation of the imaging unit 423, the arm unit 420 preferably may be configured to have six or more degrees of freedom.

The control device 440 is made up of a processor, such as a central processing unit (CPU) or a digital signal processor (DSP), for example, or a microcontroller with these processors installed onboard. By executing signal processing according to a certain program, the control device 430 controls the driving of the support arm apparatus 400.

The method of controlling the support arm apparatus 400 is not particularly limited, and the operation of the support arm apparatus 400 may be controlled by any of various known control methods, such as position control or force control. In the case of controlling the support arm apparatus 400 by position control, an input device such as a controller for operating the arm unit 420 may be provided. In the case of controlling the arm unit 420 by force control, the operation of the arm unit 420 may be controlled so that a user touches and operates the arm unit 420 directly, for example, and in response to an operation attempting to move the arm unit 420, the arm unit 420 moves in the direction of the force applied to the arm unit 420. Note that since any of various known methods may be used as the specific methods of controlling the support arm apparatus 400 by position control or force control, a detailed description is omitted herein.

Note that in the example illustrated in the drawing, the control device 440 is connected to the base unit 410 via a cable, but a component such as a control board having functions similar to the control device 440 may also be provided internally inside the base unit 410.

The above thus describes a schematic configuration of the support arm apparatus 400 according to the present embodiment with reference to FIG. 2.

(3-2. Configuration of Actuator)

A configuration of the actuator provided in each of the joint units 421a to 421f of the support arm apparatus 400 illustrated in FIG. 2 will be described with reference to FIG. 3. FIG. 3 is a cross-section diagram illustrating one exemplary configuration of an actuator according to the present embodiment. FIG. 3 illustrates a cross-section view of the actuator according to the present embodiment in the case of cutting on a plane that goes through the rotating shaft.

Note that herein, as an example, one exemplary configuration of an actuator corresponding to force control will be described. In the case of an actuator corresponding to position control, the torque sensor 428 described later may also not be provided, for example.

Figure 3:
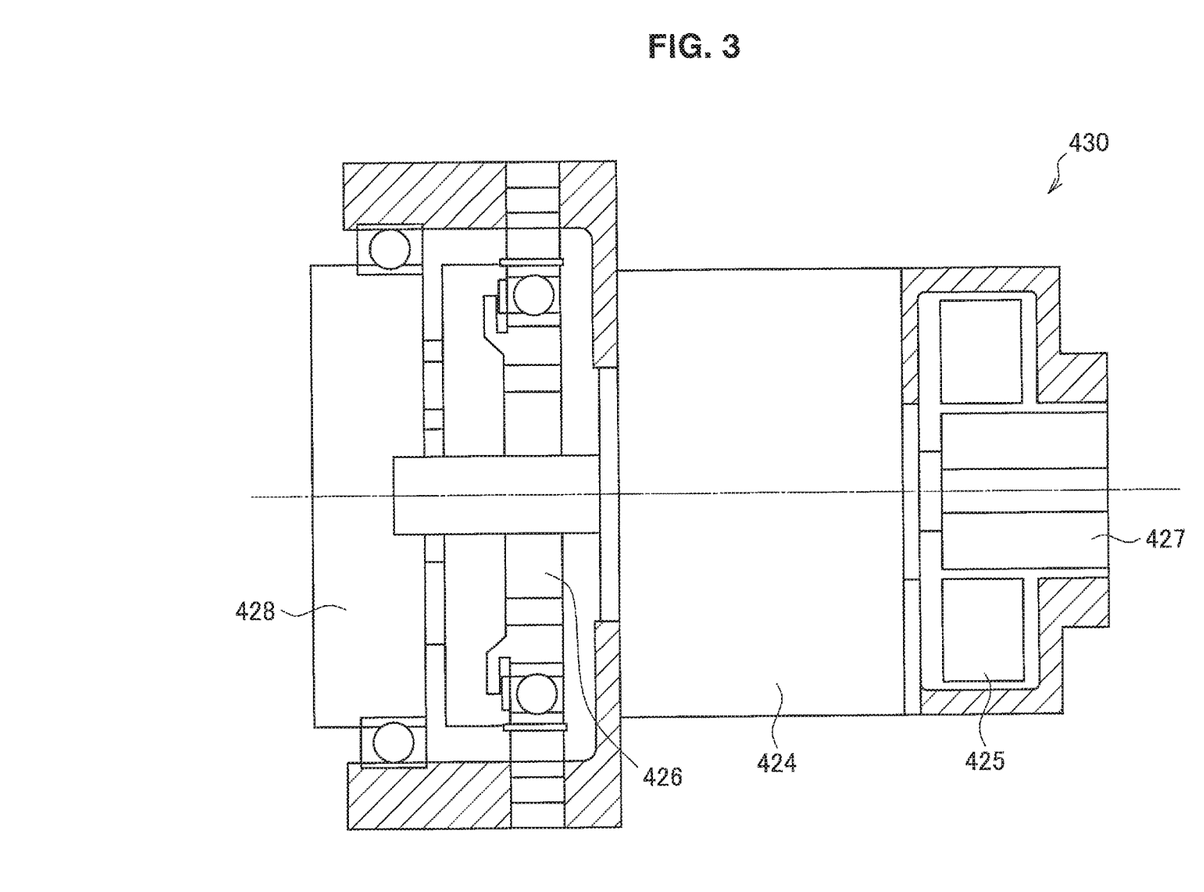
FIG. 3 is a cross-section diagram illustrating one exemplary configuration of an actuator according to the present embodiment.

Referring to FIG. 3, the actuator 430 according to the present embodiment is made up of a motor 424, a motor driver 425, a reduction gear 426, an encoder 427, and a torque sensor 428. In the actuator 430, the rotation of the motor 424 is reduced by the reduction gear 426 at a certain reduction ratio, and transmitted to other downstream members via an output shaft. As a result, the other members are driven.

The motor 424 is a driving mechanism that, in a case of being given a certain command value (current command value), causes a rotating shaft to rotate at a rotational velocity corresponding to the command value, and thereby produces driving force. For the motor 424, a brushless motor is used, for example. However, the present embodiment is not limited to such an example, and any of various known types of motors may be used as the motor 424.

The motor driver 425 is a driver circuit (driver integrated circuit (IC)) that rotationally drives the motor 424 by supplying current to the motor 424, and is able to control the rotation rate of the motor 424 by adjusting the amount of current supplied to the motor 424. The motor driver 425 drives the motor 424 by supplying the motor 424 with a current corresponding to the torque command value $\tau$ illustrated in FIG. 5 described later.

The reduction gear 426 is joined to the rotating shaft of the motor 424. The reduction gear 426 reduces by a certain reduction ratio the rotational velocity of the rotating shaft of the joined motor 424 (in other words, the rotational velocity of the input shaft), and transmits to the output shaft. In the present embodiment, the configuration of the reduction gear 426 is not limited to a specific configuration, and any of various known types of reduction gears may be used as the reduction gear 426. However, for the reduction gear 426, it is preferable to use one capable of accurately setting the reduction ratio, such as a Harmonic Drive (registered trademark), for example. In addition, the reduction ratio of the reduction gear 426 may be set appropriately according to the application of the actuator 430. For example, in the case of applying the actuator 430 to the joint units 421a to 421f of the support arm apparatus 400 as in the present embodiment, a reduction gear 426 having a reduction ratio of approximately 1:100 may be used favorably.

The encoder 427 detects the rotational angle of the input shaft (that is, the rotational angle of the motor 424). On the basis of the rotation rate of a drive shaft 429 detected by the encoder 427, and the reduction ratio of the reduction gear 426, information such as the rotational angle, the rotational angular velocity, and the rotational angular acceleration of the joint units 421a to 421f may be obtained. For the encoder 427, any of various known types of rotary encoders, such as a magnetic encoder or an optical encoder, for example, may be used. Note that in the illustrated example, the encoder 427 is provided only on the input shaft of the actuator 430, but an encoder for detecting the rotational angle of the output shaft of the actuator 430 additionally may be provided farther downstream than the reduction gear 426.

The torque sensor 428 is connected to the output shaft of the actuator 430, and detects the torque acting on the actuator 430. The torque sensor 428 detects the torque output by the actuator 430 (generated torque). Additionally, the torque sensor 428 is also able to detect external torque imparted to the actuator 430 from the outside.

The above thus describes a configuration of the actuator 430 according to the present embodiment with reference to FIG. 3. Herein, in the actuator 430 of the present embodiment, the reduction gear 426 is chosen so that the breakdown torque of the reduction gear 426 is less than the starting torque of the motor 424. Also, likewise for other component members (for example, the torque sensor 428), members having a breakdown torque that is less than the starting torque of the motor may be used similarly.

Figure 4:
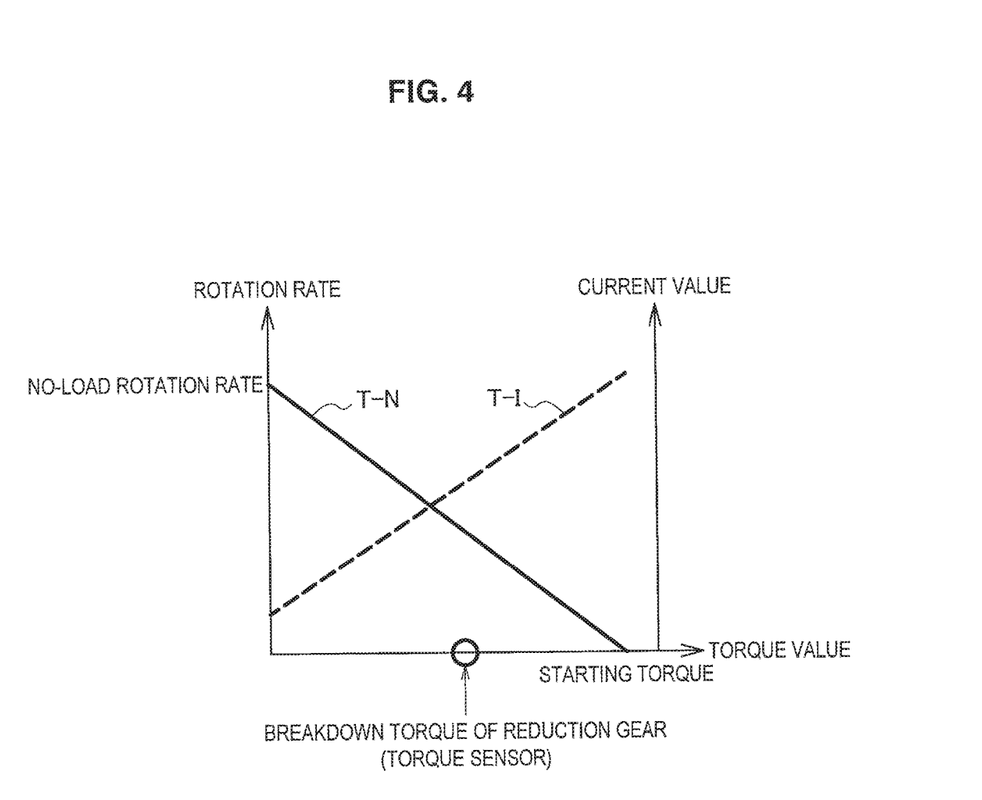
FIG. 4 is an explanatory diagram for explaining a relationship between the starting torque of a motor and the breakdown torque of a reduction gear.

The relationship between the starting torque of the motor 424 and the breakdown torque of the reduction gear 426 in the present embodiment will be described with reference to FIG. 4. FIG. 4 is an explanatory diagram for explaining the relationship between the starting torque of the motor 424 and the breakdown torque of the reduction gear 426 in the present embodiment.

FIG. 4 diagrammatically illustrates a torque-rotation rate curve (T-N curve) and a torque-current curve (T-I curve), in which the torque of the motor 424 is taken as the horizontal axis, the rotation rate is taken as one vertical axis, and the current value is taken as another vertical axis. As illustrated in FIG. 4, the point at which the rotation rate becomes zero in the T-N curve corresponds to the starting torque of the motor 424. In the present embodiment, as illustrated, a reduction gear 426 having a breakdown torque that is less than the starting torque is used. Likewise for other component members, such as the torque sensor 428, for example, a torque sensor 428 having a breakdown torque that is less than the starting torque of the motor is used similarly.

Herein, with a typical existing actuator such as those exemplified in Patent Literature 1 and 2 described earlier, for example, to prevent breakdown of the actuator, the actuator is designed so that the breakdown torque of component members, such as the reduction gear and the torque sensor, is greater than the starting torque of the motor. However, as described in (1. Investigation of typical support arm apparatus) above, since a reduction gear having a large breakdown torque is comparatively bulky, in the case of designing an actuator on the basis of such a constraint condition, it is difficult to make the actuator compact.

On the other hand, as described in (2. Overview of support arm apparatus) above, in a medical support arm apparatus, in order to perform surgeries and examinations smoothly, there is strong demand for a more compact arm unit, or in other words, a more compact actuator. In light of such circumstances, in the present embodiment, a reduction gear 426 having a breakdown torque that is less than the starting torque of the motor 424 is used. Typically, a reduction gear with a small breakdown torque is comparatively compact, and thus by using a reduction gear with a small breakdown torque, it is possible to make the actuator 430 more compact. Consequently, an actuator 430 which makes possible a more compact arm unit 420, and which may be applied favorably to a support arm apparatus 400 for medical use, may be realized. By making the arm unit 420 more compact, the work space and visual field of the surgeon can be ensured, and smoother surgeries and examinations are realized.

However, in the present embodiment, in a case of using a reduction gear 426 having a breakdown torque that is less than the starting torque of the motor 424, the driving of the actuator 430 is controlled in a state in which a limit value in accordance with the breakdown torque of the reduction gear 426 is set with respect to a control value for driving the motor 424. By conducting such control, even in a case of using a reduction gear 426 having a breakdown torque that is less than the starting torque of the motor 424, it is possible to drive the actuator 430 so that the output torque of the motor 424 does not exceed the breakdown torque of the reduction gear 426. Consequently, according to the present embodiment, it is possible to make the actuator 430 more compact, while also preventing breakdown of the reduction gear 426.

Also, in a case of using a torque sensor with a large breakdown torque, there is concern about the sensitivity of the torque sensor decreasing. On the other hand, in the present embodiment, in the actuator 430, likewise for the torque sensor 428, a torque sensor 428 having a breakdown torque that is less than the starting torque of the motor 424 may be used. Consequently, an actuator 430 capable of detecting torque more accurately may be realized.

Likewise in the case of using a torque sensor 428 having a breakdown torque that is less than the starting torque of the motor 424, similarly to the case of the reduction gear 426, the driving of the actuator 430 is controlled in a state in which a limit value in accordance with the breakdown torque of the torque sensor 428 is set with respect to a control value for driving the motor 424. By conducting such control, it becomes possible to drive the actuator 430 under conditions by which the torque sensor 428 does not break down. Consequently, according to the present embodiment, it is possible to improve the accuracy of detecting the rotational angle in the actuator 430, while also preventing breakdown of the torque sensor 428.

Also, in this way, by setting a limit value with respect to a control value for driving the motor 424, effectively the motor 424 is used in a low-torque domain, or in other words, a low-current domain and a high-rotation rate domain. Consequently, the generation of heat in the motor 424 may be reduced, while in addition, a highly responsive actuator 430 is realized.

Note that what kinds of physical quantities are to be used specifically as the control value for the motor and the limit value set with respect to the control value may be set appropriately in accordance with the driving control method of the actuator 430. For example, in the case in which force control is used, the control value for the motor may be a current value and/or a torque value given to the motor. Consequently, a limit value may be set with respect to the current value and/or with respect to the torque value. On the other hand, for example, in the case in which position control is used, the control value for the motor may be a current value given to the motor. Consequently, a limit value may be set with respect to the current value.

Hereinafter, the driving control method of the actuator 430 in the present embodiment, including the method of setting a such a limit value with respect to the control value, will be described in detail.

(4. Actuator Driving Control Method)

Figure 5:
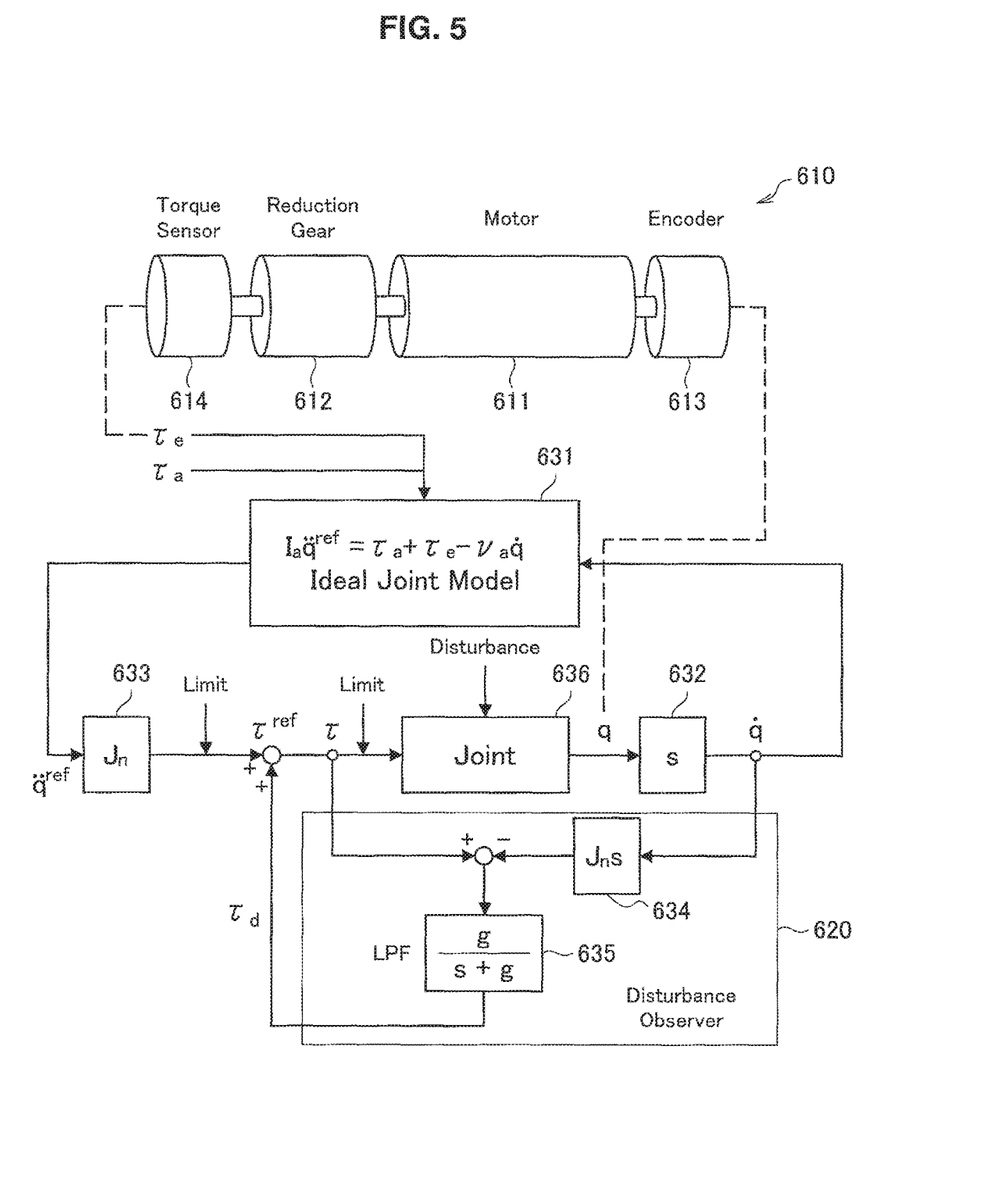
FIG. 5 is a block diagram illustrating a driving control method of an actuator according to the present embodiment.

A driving control method of the actuator 430 according to the present embodiment will be described with reference to FIG. 5. FIG. 5 is a block diagram illustrating a driving control method of the actuator 430 according to the present embodiment. Each block illustrated in FIG. 5 represents a conceptual simulation of a computing element that performs various computations related to driving control of the actuator 430. Also, the process in each block (computing element) illustrated in FIG. 5 may be realized by the control device 440 described earlier.

Note that FIG. 5 illustrates, as an example, a block diagram corresponding to the case in which the actuator 430 is driven by force control. However, the present embodiment is not limited to such an example, and the actuator 430 may also be driven by any of various other known types of control methods, such as position control. Note that the control method of the actuator 430 according to the present embodiment corresponds to setting a limit value in accordance with the breakdown torque of the reduction gear 426 with respect to a control value for the motor 424 in a typical control method of the actuator 430. Consequently, for the process until the control value is computed, a process similar to a typical control method may be conducted. For example, in the case in which the actuator 430 is driven by position control, the control method according to the present embodiment may be realized by computing a control value for the motor 424 by a method according to typical position control, and setting a limit value in accordance with the breakdown torque with respect to the computed control value.

Before describing in detail the block diagram illustrated in FIG. 4, an overview of the control method illustrated in the block diagram will be described.

The motion of each actuator 430 of the support arm apparatus 400 is modeled by the equation of second-order lag motion expressed in Formula (1) below.

[Math. 1]

$$I_a \ddot{q}^{ref} = \tau_a + \tau_e - v_a \dot{q} \tag{1}$$

Herein, q is the rotational angle of the actuator 430, $q^{ref}$ is a rotational angle target value of the actuator 430, $I_a$ is the inertial moment of the actuator 430, $\tau_a$ is the generated torque of the actuator 430, $\tau_e$ is the external torque acting on the actuator 430 from the outside, and $v_a$ is a viscous drag coefficient for the actuator 430. The above Formula (1) is a theoretical model expressing the motion of the actuator 430 in each of the joint units 421a to 421f.

With force control, the driving of the actuator 430 is controlled by using torque as the control quantity. In the case of causing the arm unit 420 to operate, the torque $\tau_a$ (generated torque $\tau_a$) to be generated by the actuator 430 in each of the joint units 421a to 421f in order to realize the desired operation may be computed. Note that since any of various existing methods may be used as the method of computing the generated torque $\tau_a$, a detailed description is reduced or omitted in this specification. For example, the generated torque $\tau_a$ may be computed by a method typically used in a control method called whole body cooperative control (a control method that controls multiple driving units cooperating with each other). For details regarding the method of computing the generated torque $\tau_a$ in whole body cooperative control, literature such as JP 2009-95959A and JP 2010-188471A, which are prior patent applications filed by the applicant, may be referenced.

Ideally, by applying the generated torque $\tau_a$ computed for each actuator 430 to Formula (1) above, a response obeying the theoretical model expressed in Formula (1) above should be realized in each actuator 430, or in other words, the desired operation should be realized in the arm unit 420.

However, in actuality, the influence of various disturbances causes error (modeling error) to occur between the actual motion in the actuator 430 and the theoretical model expressed in Formula (1) above in some cases. Modeling error may be divided roughly into error arising from mass properties, such as the mass, center of gravity, and inertia tensor of a multi-link structure (in other words, the arm unit 420 to be controlled), and error arising from factors such as friction and inertia internal to the actuator 430. Of these, the former modeling error arising from mass properties may be reduced comparatively easily during construction of the theoretical model by increasing the precision of computer-aided design (CAD) data and applying identification techniques.

On the other hand, the latter modeling error arising from factors such as friction and inertia internal to the actuator 430 is caused by phenomena which are difficult to model, such as friction in the reduction gear 426, for example, and modeling error non-negligible modeling error may still remain during construction of the theoretical model. Additionally, there is also a possibility of error occurring between the values of the inertia $I_a$ and the viscous drag coefficient $v_a$ in Formula (1) above, and these values in the actual actuator 430. Consequently, these difficult-to-model errors arising from factors such as friction and inertia internal to the actuator 430 may become disturbances in the driving control of the actuator 430. Thus, because of the influence of such disturbances, in actuality, cases occur in which the motion of the actuator does not respond exactly like the theoretical model expressed in Formula (1) above, or in other words, the desired operation is not realized.

Accordingly, in the present embodiment, an active control system is added to the actuator 430 to thereby correct the response of the actuator 430 so as to perform ideal response obeying the theoretical model expressed in Formula (1) above. Note that controlling the driving of the actuator 430 so that the actuators 430 of the support arm apparatus 400 (that is, the joint units 421a to 421f) perform ideal response as expressed in Formula (1) above in this way is designated ideal joint control in the present embodiment. The block diagram illustrated in FIG. 4 is an illustration of a series of processes for such ideal joint control with respect to the actuator 430 in one joint unit among the joint units 421a to 421f of the support arm apparatus 400.

Hereinafter, the driving control method of the actuator 430 will be described in detail with reference to FIG. 4. Referring to FIG. 4, the actuator 610 illustrates a simulation of the functions of the actuator 430 illustrated in FIG. 3, for example. In FIG. 4, a motor 611, a reduction gear 612, an encoder 613, and a torque sensor 614 are illustrated as component members of the actuator 610. These respectively correspond to the motor 424, the reduction gear 426, the encoder 427, and the torque sensor 428 illustrated in FIG. 3.

The computing element 631 is a computing element that perform computation in accordance with the ideal joint model of the actuator 610 (joint units 421a to 421f) expressed in Formula (1) above. The computing element 631 is able to take the generated torque $\tau_a$, the external torque $\tau_e$, and the rotational angular velocity (the first derivative of the rotational angle q) as input, and output the rotational angular acceleration target value (the second derivative of the rotational angle target value $q^{ref}$) expressed on the left side of Formula (1) above.

Herein, The actuator 610 performing response obeying the ideal model expressed in Formula (1) above means nothing other than that when the right side of Formula (1) above is given, the rotational angular acceleration on the left side is achieved. However, as above, ideal response obeying Formula (1) above actually is not produced sometimes, due to the influence of disturbances. Accordingly, in the present embodiment, a disturbance observer 620 is introduced. A process is conducted in which a disturbance estimate value $\tau_d$, which is an estimate value of the torque arising from a disturbance by the disturbance observer 620, is computed, and the disturbance estimate value $\tau_d$ is used to correct the calculation result by the computing element 631.

Hereinafter, specific processes will be described in order. First, the generated torque $\tau_a$ for realizing a desired operation computed on the basis of a method used in typical force control, and the external torque $\tau_e$ detected by the torque sensor 614, are input into the computing element 631. Meanwhile, by inputting the rotational angle q of the actuator 610 detected by the encoder 613 into a computing element 632 that performs differential computations, the rotational angular velocity (the first derivative of the rotational angle q) of the actuator 610 is computed. By inputting the rotational angular velocity computed by the computing element 632, in addition to the generated torque $\tau_a$ and the external torque $\tau_e$ above, into the computing element 631, the rotational angular acceleration target value (the second derivative of $q^{ref}$) is computed by the computing element 631. The computed rotational angular acceleration target value is input into a computing element 633.

The computing element 633 is a computing element that computes the torque generated in the actuator 610, on the basis of the rotational angular acceleration of the actuator 610. In the present embodiment, specifically, the computing element 633 obtains a torque target value $\tau^{ref}$ by multiplying the rotational angular acceleration target value computed by the computing element 631 by the nominal inertia $J_n$ of the actuator 610. In ideal response, the actuator 610 is driven so as to output the torque target value $\tau_{ref}$, and thus the desired operation should be realized, but as described earlier, the influence of disturbances and the like is produced in the actual response in some cases. Consequently, in the present embodiment, the torque target value $\tau^{ref}$ is corrected using the disturbance estimate value $\tau_d$ computed by the disturbance observer 620.

The configuration of the disturbance observer 620 will be described. The disturbance observer 620 computes the disturbance estimate value $\tau_d$, on the basis of the torque command value $\tau$ and the rotational angular velocity computed from the rotational angle q of the actuator 610 detected by the encoder 613. Herein, the torque command value $\tau$ is the command value ultimately given to the actuator 610 after the influence of disturbances is corrected. In other words, in the control system illustrated in FIG. 5, the actuator 610 is driven so as to output the torque command value $\tau$. For example, in the case in which the disturbance estimate value $\tau_d$ is approximately zero, the torque command value $\tau$ becomes a value approximately equal to the torque target value $\tau^{ref}$.

Specifically, the disturbance observer 620 is made up of a computing element 634 and a computing element 635. The computing element 634 is a computing element that computes the torque generated in the actuator 610, on the basis of the rotational angular velocity of the actuator 610. Input into the computing element 634 is the rotational angular velocity computed by the computing element 632 on the basis of the rotational angle q detected by the encoder 613. The computing element 634 performs computations expressed by a transfer function $J_{nS}$ on the input rotational angular velocity, or in other words, finds the rotational angular acceleration by taking the derivative of the rotational angular velocity, and additionally multiplies the computed rotational angular acceleration by the nominal inertia $J_n$, and thereby computes an estimate value of the torque (torque estimate value) actually acting on the actuator 610.

Inside the disturbance observer 620, by taking the difference between the torque estimate value and the torque command value τ, the value of the torque due to disturbances, that is, the disturbance estimate value $\tau_d$, is estimated. Specifically, the disturbance estimate value $\tau_d$ is the difference between the torque command value τ from the control in the previous step, and the torque estimate value from the control in the current step. Since the torque estimate value computed by the computing element 634 is based on an actual measured value, and the torque command value τ computed by the computing element 633 is based on an ideal theoretical model of the actuator 610 computed by the computing element 631, by taking the difference between the two, the influence of disturbances not taken into account by the theoretical model above can be estimated.

The computing element 635 is a computing element provided to prevent divergence of the system, and includes the function of a low-pass filter (LPF). The computing element 635 performs the computations expressed by the transfer function g/(s+g) to thereby output only the low-frequency component with respect to an input value, and stabilize the system. The difference value between the torque estimate value and the torque target value $\tau^{ref}$ computed by the computing element 634 is input into the computing element 635, and the low-frequency component thereof is computed as the disturbance estimate value $\tau_d$.

After the disturbance estimate value $\tau_d$ is computed by the disturbance observer 620, the disturbance estimate value $\tau_d$ is added to the theoretical value, that is, the torque target value $\tau^{ref}$, to thereby compute the torque value to ultimately generate in the actuator 610, that is, the torque command value τ. The computed torque command value τ is input into a block 636 representing a joint unit. The block 636 expresses a simulation of the joint units 421a to 421f (in other words, the actuator 610). In the block 636, the actuator 610 is driven on the basis of the torque command value τ. Specifically, in the block 636, by converting the torque command value τ into a corresponding current value (current command value), and applying this current command value to the motor 611, the actuator 610 is driven so as to output torque corresponding to the torque command value τ.

At this point, as described above, in the present embodiment, the driving of the actuator 610 is controlled so that the control value for driving the motor 611 becomes less than or equal to a control value corresponding to the breakdown torque of the reduction gear 612. In the case of the example illustrated in FIG. 5, control values for driving the motor 611 may be the torque command value τ and the torque target value $\tau^{ref}$, as well as a current command value and a current target value obtained by converting these to current values.

In this way, in the case in which force control is used, a current value and a torque value may be computed as control values for driving the motor 611. In other words, in the present embodiment, the driving of the actuator 610 is controlled in a state in which a limit value in accordance with the breakdown torque of the reduction gear 612 is set with respect to at least one of a current value and a torque value.

As an example, a case in which a limit value is set with respect to a current value will be described. The torque command value τ and the current command value described above exist in a relationship whereby the torque command value τ is computed by multiplying the current command value by a torque constant. In actuality, in the block 636 illustrated in FIG. 5 (in other words, the actuator 610), in a case in which the torque command value τ is given, this relationship is used to control the current command value given to the motor 611 by classical PID control, and thus controls is conducted so that the torque of the motor 611 converges on the torque command value τ.

For example, in a case in which a limit value is set with respect to the current value, a limit value in accordance with the breakdown torque of the reduction gear 612 is set as an upper-limit value on the current command value in the PID control. Subsequently, the driving of the motor 611 is controlled so that the current command value does not exceed the upper-limit value (limit value). For the limit value, factors such as the N-T characteristics of the motor 611 and the fatigue failure characteristics of the reduction gear 612 illustrated in FIG. 6 described later are taken into account to set a value so that the generated torque generated by the motor 611 does not exceed the breakdown torque of the reduction gear 612. With this arrangement, structural breakdown of the reduction gear 612 due to the generated torque generated by the motor 611 is avoided.

As another example, a case in which a limit value is set with respect to a torque value will be described. In this case, for example, a limit value is set with respect to the torque target value $\tau^{ref}$ described above. Specifically, a limit value in accordance with the breakdown torque of the reduction gear 612 is set as an upper-limit value on the torque target value $\tau^{ref}$, and the driving of the motor 611 is controlled so that the torque target value $\tau^{ref}$ does not exceed this upper-limit value (limit value). For the limit value, factors such as the N-T characteristics of the motor 611 and the fatigue failure characteristics of the reduction gear 612 illustrated in FIG. 6 described later are taken into account to set a value so that the generated torque generated by the motor 611 does not exceed the breakdown torque of the reduction gear 612. With this arrangement, structural breakdown of the reduction gear 612 due to the generated torque generated by the motor 611 is avoided.

Note that in this example, when a limit value is set with respect to a torque value, the limit value is set with respect to the torque target value $\tau^{ref}$, but a limit value may also be set with respect to the torque command value τ. However, as described later, with force control, generated torque that is greater than the target value may also be produced in the motor 611 while the control is stabilizing. Typically, to improve the responsiveness of the motor 611, the torque command value τ is often a greater value than the torque target value $\tau^{ref}$. Thus, depending on the strength of the reduction gear 612, if the torque command value τ is loaded steadily, there is an increased possibility of the reduction gear 612 breaking down. Consequently, when setting a limit value with respect to the torque value, to avoid imposing a large load steadily, it is preferable to set a limit value with respect to the torque target value $\tau^{ref}$ like the example above. However, if the limit value is set appropriately, obviously a limit value may be set with respect to the torque command value τ. Current values may be considered to be similar, but as described later, for current values, a physical limit may be imposed so that a current exceeding a limit value may not be applied to the motor 611. Thus, a limit value may be set favorably on the current command value corresponding to the torque command value τ.

Herein, the method of setting a limit value with respect to a current value and the method of setting a limit value with respect to a torque value may be based on different approaches.

For example, for the torque value, a comparatively small torque value compared to the breakdown torque of the reduction gear 612 may be set as the limit value. This is to account for overshoot of the generated torque by the motor 611 while the control is stabilizing.

With force control, the driving of the motor 611 is controlled so that the generated torque generated by the motor 611 converges on a target value, and at this point, generated torque that is greater than the target value may also be produced while the control is stabilizing. Consequently, in the case in which a value that is approximately the same as the breakdown torque of the reduction gear 612 is set as the limit value with respect to the torque target value $\tau^{ref}$, for example, if a value that is equal to the limit value or close to the limit value is given as the torque target value $\tau^{ref}$, there is a possibility of the generated torque generated by the motor 611 exceeding the breakdown torque by overshooting while the control is stabilizing. Thus, for the limit value with respect to the torque value, preferably a torque value that is less than the breakdown torque may be set, so that the generated torque generated by the motor 611 does not exceed the breakdown torque of the reduction gear 612 even in a case in which overshoot occurs.

On the other hand, for example, for a current value, a current value corresponding to the breakdown torque of the reduction gear 612 may be set as the limit value. However, in this case, for the current value, a physical limit may be imposed so that a current exceeding the limit value cannot be applied to the motor 611. In this way, the setting of a limit value with respect to a current value may also be considered to be physically placing a limit so that the generated torque generated by the motor 611 does not exceed the breakdown torque of the reduction gear 612. By controlling the current value in this way, breakdown of the reduction gear 612 may be prevented more reliably.

In the present embodiment, with regard to the setting of a limit value with respect to a current value and the setting of a limit value with respect to a torque value described above, only one of the two may be conducted, or both may be conducted. Even in the case in which a limit value is set with respect to only one of the current value and the torque value, by appropriately setting a limit value on the basis of the approaches described above, it becomes possible to control the driving of the actuator 610 so that the generated torque generated by the motor 611 does not exceed the breakdown torque of the reduction gear 612.

However, in the case in which force control is conducted, if a limit value is set with respect to only the current value, there is a possibility of the control becoming unstable. This is because with force control, the driving of the motor 611 is controlled by taking a torque value as the target value, and thus the control values which are computed as described with reference to FIG. 5 and given to the motor 611 are also torque values (for example, the torque command value τ and the torque target value $\tau^{ref}$ described above). Consequently, in the case in which force control is conducted, by setting a limit value with respect to the actual control value, that is, a torque value, more stable control may be realized.

On the other hand, in the case in which a limit value is set with respect to only a torque value, there is a possibility of the generated torque generated by the motor 611 exceeding the breakdown torque of the reduction gear 612, such as in the case in which the amount of overshoot is greater than expected, or the case in which an unanticipated large external force is imparted to the actuator 610, for example.

Consequently, if factors such as the stability of control and the danger of the generated torque generated by the motor 611 exceeding the breakdown torque of the reduction gear 612 as described above are taken into account, it is preferable for limit values to be set with respect to both a current value and a torque value. In this case, on the basis of the above approaches, for example, a lower value that may allow for excess due to overshoot may be set as the limit value on the torque value, whereas a higher value that does not allow excess may be set as the limit value on the current value. This arrangement makes it possible to control the generated torque generated by the motor 611 so that the breakdown torque of the reduction gear 612 is not exceeded while still allowing for overshoot, and thus more stable control may be realized while also preventing breakdown of the reduction gear 612, or in other words, the actuator 610. In this way, by providing a difference between the limit value with respect to the torque value and the limit value with respect to the current value, it becomes possible to prevent breakdown of the reduction gear 612 more reliably, while also ensuring control stability.

The above thus describes a driving control method of the actuator 610 according to the present embodiment, with reference to FIG. 5. As described above, according to the present embodiment, the motor 611 may be driven in a state in which a limit value is set with respect to a control value for the motor 611, that is, a current value and/or a torque value. At this point, for the limit value, factors such as the N-T characteristics of the motor 611 and the fatigue failure characteristics of the reduction gear 612 are taken into account to set a value so that the generated torque generated by the motor 611 does not exceed the breakdown torque of the reduction gear 612. Consequently, breakdown of the actuator 610 may be restrained favorably.

Note that in the above description, in the case in which a reduction gear 612 having a breakdown torque that is less than the starting torque of the motor 611 is used, driving control of the actuator 610 so that breakdown of the reduction gear 612 may be prevented is described, but likewise for other component members, such as the torque sensor 614, for example, the driving of the actuator 610 may be controlled similarly in a state in which a limit value corresponding to the breakdown torque of these component members is set with respect to at least one of a current value and a torque value. With this arrangement, breakdown of these component members may also be prevented favorably.

(5. Breakdown Torque)

Figure 6:
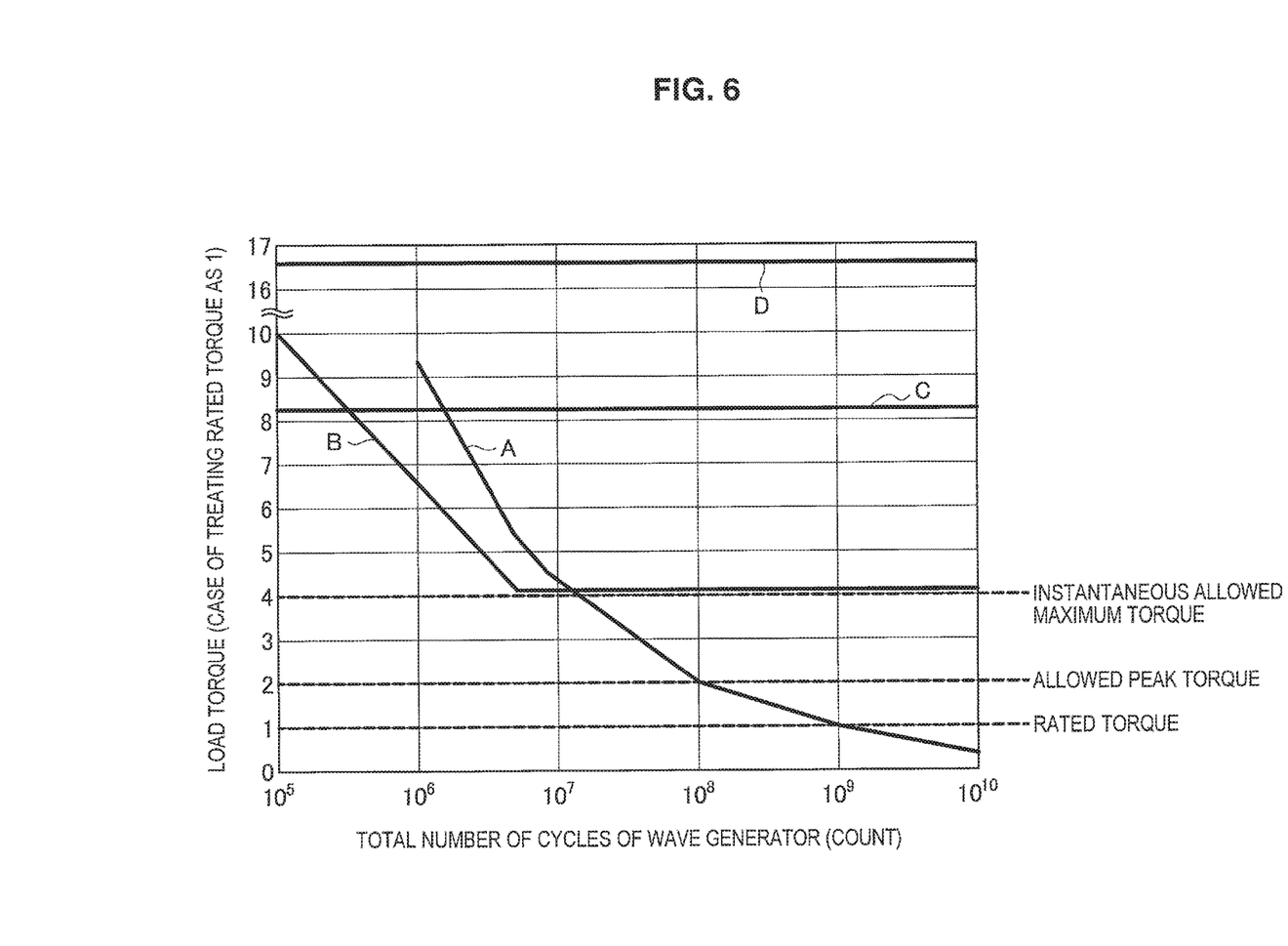
FIG. 6 is an explanatory diagram for explaining the concept of breakdown torque in the present embodiment.

The concept of breakdown torque in the present embodiment will be described with reference to FIG. 6. FIG. 6 is an explanatory diagram for explaining the concept of breakdown torque in the present embodiment.

FIG. 6 illustrates the fatigue failure characteristics of the reduction gear 426 according to the present embodiment. In FIG. 6, the fatigue failure characteristics in a certain Harmonic Drive are illustrated as an example. In the diagram, the horizontal axis is the total number of cycles of the wave generator of the reduction gear 426, while the vertical axis is the load torque when the rated torque is taken to be 1. The total number of cycles of the wave generator of the reduction gear 426 plotted on the horizontal axis may be considered to correspond to the operating time of the reduction gear 426. In this way, the fatigue failure characteristics of the reduction gear 426 illustrated in FIG. 6 correspond to what is called an S-N diagram.

As illustrated, for the reduction gear 426, various curves related to fatigue failure are defined. In the diagram, Curve A is a curve representing the fatigue failure characteristics of the wave generator. Curve B is a curve representing the fatigue failure characteristics of the bottom of the flexspline. Curve C is a curve representing the breakdown limit (also known as the breakdown strength) at which tooth jumping called ratcheting occurs. Curve D is a curve representing the breakdown limit (also known as the breakdown strength) at which buckling occurs. The characteristic diagram illustrated in FIG. 6 illustrates that the reduction gear 426 breaks down in a case in which one of these curves is exceeded due to the load torque and the cumulative total number of cycles of the wave generator.

Additionally, in the reduction gear 426, on the basis of these fatigue failure characteristics, an allowed peak torque (in the illustrated example, the torque at which the load torque=2) and an instantaneous allowed maximum torque (in the illustrated example, the torque at which the load torque=4) are defined. The allowed peak torque is the torque which may be allowed to be loaded momentarily when starting and stopping from the perspective of stable usage, while the instantaneous allowed maximum torque is the torque which is not allowed to be loaded for even an instant from the same perspective of stable usage.

The allowed peak torque and the instantaneous allowed maximum torque may be set appropriately by someone such as the designer of the actuator 430, taking into account the fatigue life demanded of the reduction gear 426, on the basis of the illustrated fatigue failure characteristics of the reduction gear 426, for example. Alternatively, in the case in which a commercially available reduction gear 426 is used, typically the allowed peak torque and the instantaneous allowed maximum torque, or torque values based on the same, are stipulated by the manufacturer who produces the reduction gear 426.

In FIG. 6, the fatigue failure characteristics of the reduction gear 426 are illustrated as an example, but similar fatigue failure characteristics corresponding to an S-N diagram may be acquired likewise for other component members constituting the actuator 430. In the present embodiment, the breakdown torque of each component member may be set appropriately by taking into account the fatigue life demanded of each of these component members, on the basis of the fatigue failure characteristics for each component member as exemplified in FIG. 6. For example, in the case in which a torque sensor 428 having a breakdown torque that is less than the starting torque of the motor 424 is used, the breakdown torque of the torque sensor 428 may be set on the basis of the fatigue failure characteristics of the torque sensor 428.

For example, in the case of the illustrated example, the instantaneous allowed maximum torque may be used as the breakdown torque of the reduction gear 426. In this case, a limit value by which the generated torque generated by the motor 424 becomes less than or equal to the instantaneous allowed maximum torque may be set as the limit value (upper-limit value) with respect to a current value and/or a torque value.

However, as described above, limit values with respect to a current value and a torque value may be set on the basis of different approaches. For example, as a limit value on a current value, a current value corresponding to the instantaneous allowed maximum torque may be set as the limit value. Subsequently, control is conducted so that a current greater than the limit value is not applied to the motor 424. On the other hand, for example, as a limit value on a torque value, a torque value lower than the instantaneous allowed maximum torque that accounts for overshoot during control may be set as the limit value.

The above thus describes the concept of breakdown torque in the present embodiment, with reference to FIG. 6.

Herein, as described above, the breakdown torque of the reduction gear 426 is closely related to the operating time and load torque history of the reduction gear 426. Likewise for other component members of the actuator 430, the breakdown torque similarly may depend on the load torque and time (or number of cycles) that torque has been loaded. Consequently, in the driving control of the actuator 430 according to the present embodiment, a history of torque values loaded on each component member of the actuator 430 may be acquired, and in accordance with the history, the value of the breakdown torque set with respect to each component member may be modified appropriately. With this arrangement, a more appropriate value is used as the breakdown torque of each component member, thereby making it possible to set a limit value with respect to a current value and/or a torque value more appropriately.

Also, as above, since the breakdown torque of each component member of the actuator 430 is closely related to the load torque and the time (or number of cycles) that torque has been loaded, by acquiring a history of torque values loaded on each component member of the actuator 430, for example, the allowed magnitude of load torque and load time (or number of load cycles) of that load torque until the component member breaks down may be ascertained. Consequently, in the driving control of the actuator 430 according to the present embodiment, on the basis of such ascertained information, a limit value with respect to a current value and/or a torque value may also be set to a higher-than-normal value, insofar as the component member does not break down.

For example, as described above, a limit value with respect to a torque value ordinarily is set to a value that is less than the breakdown torque, so that even if overshoot occurs, the generated torque generated by the motor 424 does not exceed the breakdown torque of the component member being considered. However, in a case in which the relevant component member is judged, from the history of the load torque on that component member, to have an adequate margin until breakdown, the limit value with respect to the torque value may be raised. With this arrangement, the generated torque generated by the motor 424 can be increased, thereby making it possible to increase the output of the actuator 430 temporarily. However, as a result of the limit value being raised, excessive torque which ordinarily may not be loaded becomes loaded on the component member. Consequently, at a time when such excessive torque has been loaded for a certain amount of time or a certain number of cycles, the limit value may be reverted back to the ordinary value.

In this way, by flexibly modifying the breakdown torque as well as a limit value with respect to a current value and/or a torque value insofar as each component member does not break down on the basis of a history of the load torque on each component member, driving control of the actuator 430 with a higher degree of freedom becomes possible, while also preventing breakdown more reliably.

(6. Supplement)

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)
An actuator, including:
a motor; and a reduction gear having a breakdown torque that is less than a starting torque of the motor, in which
a limit value in accordance with the breakdown torque of the reduction gear is set with respect to a control value for driving the motor.

(2)
The actuator according to (1), in which
the control value is a current value, and
a current value by which the breakdown torque of the reduction gear becomes less than or equal to a generated torque generated by the motor is set as the limit value with respect to the control value.

(3)
The actuator according to (2), in which
a current value applied to the motor is controlled so as not to exceed the limit value.

(4)
The actuator according to any one of (1) to (3), in which
the control value is a torque value, and
a torque value by which the breakdown torque of the reduction gear becomes less than or equal to a generated torque generated by the motor is set as the limit value with respect to the control value.

(5)
The actuator according to (4), in which
the limit value is set while also taking into account an amount of overshoot of the generated torque generated by the motor.

(6)
The actuator according to (1), in which
the control value is a torque value and a current value, and
a torque value and a current value by which the breakdown torque of the reduction gear becomes less than or equal to a generated torque generated by the motor are set respectively as the limit value with respect to the torque value and the current value which are the control value.

(7)
The actuator according to any one of (1) to (5), in which
a value of the breakdown torque of the reduction gear is set as a torque value by which a certain fatigue life is ensured, on a basis of fatigue failure characteristics of the reduction gear.

(8)
The actuator according to any one of (1) to (6), in which
a value of the breakdown torque of the reduction gear is modified in accordance with a history of torque loaded on the reduction gear, on a basis of fatigue failure characteristics of the reduction gear.

(9)
The actuator according to any one of (1) to (7), further including:
a torque sensor having a breakdown torque that is less than a starting torque of the motor, in which
a limit value in accordance with the breakdown torque of the torque sensor is additionally set with respect to the control value.

(10)
A medical support arm apparatus, including:
an arm unit made up of a plurality of joint units; and
a medical tool provided on a front edge of the arm unit, in which
an actuator provided in the joint unit includes a motor, and a reduction gear having a breakdown torque that is less than a starting torque of the motor, and
a limit value in accordance with the breakdown torque of the reduction gear is set with respect to a control value for driving the motor.

(11)
The medical support arm apparatus according to (10), in which
the medical tool provided on the front edge of the arm unit is an observation unit for observing a surgical site.

(12)
The medical support arm apparatus according to (10), in which
the medical tool provided on the front edge of the arm unit is a pair of forceps.

(13)
The medical support arm apparatus according to any one of (10) to (12), in which
driving of the actuator provided in the joint unit is controlled by force control.

REFERENCE SIGNS LIST 400, 510 support arm apparatus (observation device)
410, 511 base unit
420, 512 arm unit
421a to 421f, 513a to 513c joint units
423, 515 imaging unit
430, 610 actuator
424, 611 motor
426, 612 reduction gear
427, 613 encoder
428, 614 torque sensor
440 control device

The invention claimed is:

1. An actuator, comprising:
a motor;
a reduction gear having a breakdown torque that is less than a starting torque of the motor; and
a control device configured to set a limit value with respect to a control value to drive the motor based on the breakdown torque of the reduction gear.

2. The actuator according to claim 1,
wherein the control value is a current value applied to the motor, and
wherein the control device is further configured set, as the limit value, the current value applied to the motor to generate a torque by the motor that is less than or equal to the breakdown torque of the reduction gear.

3. The actuator according to claim 2, wherein the control device is configured to control the current value applied to the motor such that the current value is less than or equal to the limit value.

4. The actuator according to claim 1,
wherein the control value is a torque value, and
wherein the control device is further configured to set, as the limit value, the torque value to generate a torque by the motor that is less than or equal to the breakdown torque of the reduction gear.

5. The actuator according to claim 4, wherein the control device is further configured to set the limit value based on an amount of overshoot of the generated torque.

6. The actuator according to claim 1,
wherein the control value is at least one of a torque value or a current value applied to the motor, and
wherein the control device is further configured to set, as the limit value, the at least one of the torque value or the current value applied to the motor to generate a torque that is less than or equal to the breakdown torque of the reduction gear.

7. The actuator according to claim 1, wherein the control device is further configured to set as a torque value, a value of the breakdown torque of the reduction gear that ensures a certain fatigue life, based on fatigue failure characteristics of the reduction gear.

8. The actuator according to claim 1, wherein the control device is further configured to modify a value of the breakdown torque of the reduction gear based on a history of torque of the reduction gear and fatigue failure characteristics of the reduction gear.

9. The actuator according to claim 1, further comprising:
a torque sensor having a breakdown torque that is less than the starting torque of the motor,
wherein the control device is further configured to set the limit value with respect to the control value based on the breakdown torque of the torque sensor.

10. A medical support arm apparatus, comprising:
an arm unit having a plurality of joint units;
a medical tool on a front edge of the arm unit; and
an actuator in at least one joint unit of the plurality of joint units,
wherein the actuator includes:
a motor;
a reduction gear having a breakdown torque that is less than a starting torque of the motor; and
a control device configured to set a limit value with respect to a control value to drive the motor based on the breakdown torque of the reduction gear.

11. The medical support arm apparatus according to claim 10, wherein the medical tool is an observation unit for observation of a surgical site.

12. The medical support arm apparatus according to claim 10, wherein the medical tool is a pair of forceps.

13. The medical support arm apparatus according to claim 10, wherein the control device is further configured to control driving of the actuator based on force control.

14. The medical support arm apparatus according to claim 10, wherein the control device is further configured to control driving of the actuator based on position control.

15. The medical support arm apparatus according to claim 11, wherein the observation unit is an endoscope.

16. The medical support arm apparatus according to claim 11, wherein the observation unit is a microscope.

* * * * *